United States Patent
Pusch

(10) Patent No.: US 8,251,928 B2
(45) Date of Patent: Aug. 28, 2012

(54) METHOD FOR CARRYING OUT A FUNCTIONAL ANALYSIS OF AN ARTIFICIAL EXTREMITY

(75) Inventor: Martin Pusch, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 710 days.

(21) Appl. No.: 12/091,883

(22) PCT Filed: Oct. 10, 2006

(86) PCT No.: PCT/DE2006/001767
§ 371 (c)(1),
(2), (4) Date: Apr. 28, 2008

(87) PCT Pub. No.: WO2007/048374
PCT Pub. Date: May 3, 2007

(65) Prior Publication Data
US 2008/0287834 A1    Nov. 20, 2008

(30) Foreign Application Priority Data

Oct. 26, 2005 (DE) .......................... 10 2005 051 496

(51) Int. Cl.
*A61B 5/103* (2006.01)
*A61B 5/117* (2006.01)
*A61F 2/80* (2006.01)
*G01S 7/40* (2006.01)
*G12B 13/00* (2006.01)

(52) U.S. Cl. ............. 600/595; 606/88; 623/38; 73/1.75; 73/1.77

(58) Field of Classification Search ................... 600/585, 600/595; 606/88; 623/38; 73/1.75, 1.77
See application file for complete search history.

(56) References Cited

U.S. PATENT DOCUMENTS

| | | | | |
|---|---|---|---|---|
| 4,911,023 A | * | 3/1990 | Izumi et al. | 73/862.044 |
| 5,127,420 A | * | 7/1992 | Horvath | 600/595 |
| 5,413,611 A | * | 5/1995 | Haslam et al. | 623/25 |
| 5,733,292 A | * | 3/1998 | Gustilo et al. | 606/88 |

(Continued)

FOREIGN PATENT DOCUMENTS

DE    19754690    7/1999

(Continued)

OTHER PUBLICATIONS

International Search Report for PCT/DE2006/001767 mailed Mar. 5, 2007, 3 pgs.

*Primary Examiner* — Sean Dougherty
(74) *Attorney, Agent, or Firm* — Holland & Hart LLP

(57) ABSTRACT

A method for carrying out a functional analysis on a person equipped with an artificial extremity having adjustable settings. The method includes the steps of providing a sensor assembly configured as a replacement for a part of the artificial extremity and installing the sensor assembly in place of the part. Forces, accelerations and/or torques are then measured with the sensor assembly during use of the artificial extremity by the person and the settings of the artificial extremity are optimized based on these measurements. The sensor assembly is removed and the replaced part is installed back into the artificial extremity, while retaining the optimized settings. In one embodiment, the artificial extremity is a leg prosthesis having an artificial knee joint with a rotational adaptor mounted above it. The sensor assembly then replaces the rotational adaptor.

10 Claims, 4 Drawing Sheets

U.S. PATENT DOCUMENTS

| | | | | |
|---|---|---|---|---|
| 5,800,565 A * | 9/1998 | Biedermann | | 623/38 |
| 6,051,026 A * | 4/2000 | Biedermann et al. | | 623/38 |
| 6,423,098 B1 * | 7/2002 | Biedermann | | 623/24 |
| 6,679,920 B2 * | 1/2004 | Biedermann et al. | | 623/24 |
| 6,755,870 B1 * | 6/2004 | Biedermann et al. | | 623/24 |
| 6,834,752 B2 * | 12/2004 | Irby et al. | | 192/81 C |
| 6,905,519 B2 * | 6/2005 | Swanson, Sr. | | 623/36 |
| 6,908,488 B2 * | 6/2005 | Passivaara et al. | | 623/24 |
| 6,918,308 B2 * | 7/2005 | Biedermann et al. | | 73/862.629 |
| 7,150,762 B2 * | 12/2006 | Caspers | | 623/33 |
| 7,485,152 B2 * | 2/2009 | Haynes et al. | | 623/24 |
| 7,769,422 B2 * | 8/2010 | DiSilvestro et al. | | 600/407 |
| 7,886,618 B2 * | 2/2011 | Macomber et al. | | 73/862.044 |
| 2002/0161451 A1 * | 10/2002 | Biedermann et al. | | 623/27 |
| 2003/0029247 A1 * | 2/2003 | Biedermann et al. | | 73/768 |
| 2003/0062241 A1 * | 4/2003 | Irby et al. | | 192/81 C |
| 2003/0125814 A1 * | 7/2003 | Paasivaara et al. | | 623/44 |
| 2004/0059433 A1 * | 3/2004 | Slemker et al. | | 623/38 |
| 2005/0010139 A1 * | 1/2005 | Aminian et al. | | 600/595 |
| 2005/0166685 A1 * | 8/2005 | Boiten | | 73/862.191 |
| 2005/0267600 A1 * | 12/2005 | Haberman et al. | | 623/38 |
| 2005/0273170 A1 * | 12/2005 | Navarro et al. | | 623/17.13 |
| 2006/0195197 A1 * | 8/2006 | Clausen et al. | | 623/24 |
| 2006/0206214 A1 * | 9/2006 | Clausen et al. | | 623/24 |
| 2007/0010772 A1 * | 1/2007 | Ryan | | 602/26 |
| 2007/0073196 A1 * | 3/2007 | Tanaka et al. | | 600/595 |
| 2007/0209220 A1 * | 9/2007 | Murphy | | 33/512 |
| 2007/0239165 A1 * | 10/2007 | Amirouche | | 606/86 |
| 2008/0140221 A1 * | 6/2008 | Macomber et al. | | 623/27 |
| 2008/0146969 A1 * | 6/2008 | Kurtz | | 600/595 |
| 2008/0276725 A1 * | 11/2008 | Pusch | | 73/862.041 |
| 2009/0005708 A1 * | 1/2009 | Johanson et al. | | 600/587 |
| 2010/0328098 A1 * | 12/2010 | Stein et al. | | 340/870.3 |

FOREIGN PATENT DOCUMENTS

| | | | |
|---|---|---|---|
| DE | 10139333 A1 | | 3/2003 |
| EP | 1285640 | | 2/2003 |
| GB | 2149309 A | * | 6/1985 |
| JP | 05212070 A | * | 8/1993 |
| JP | 2003070817 A | * | 3/2003 |
| WO | 95/31949 | | 4/1995 |
| WO | 01/17466 A2 | | 8/2000 |
| WO | 2004/041132 A2 | | 11/2003 |
| WO | WO 2004041132 A2 | * | 5/2004 |
| WO | WO 2007003169 A2 | * | 1/2007 |

\* cited by examiner

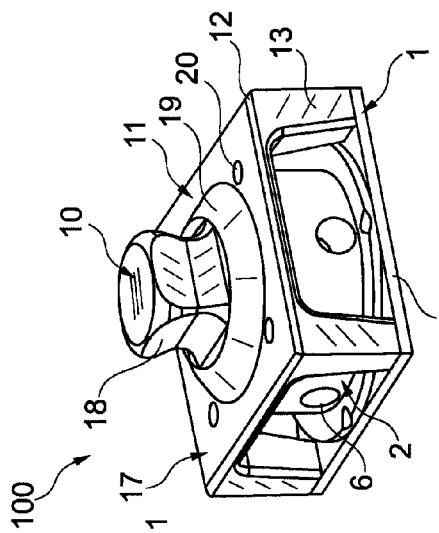
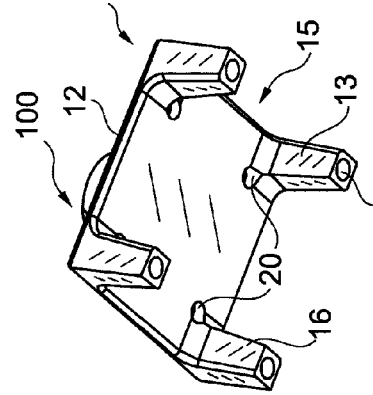
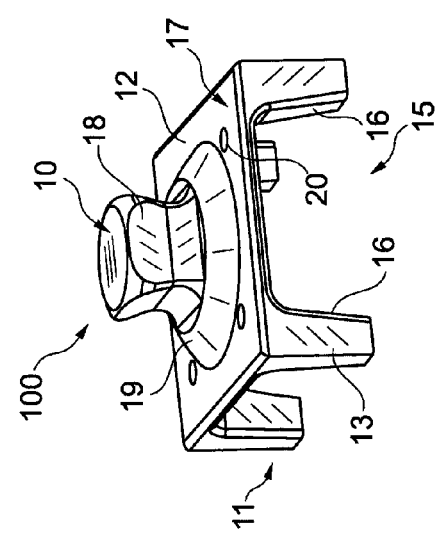
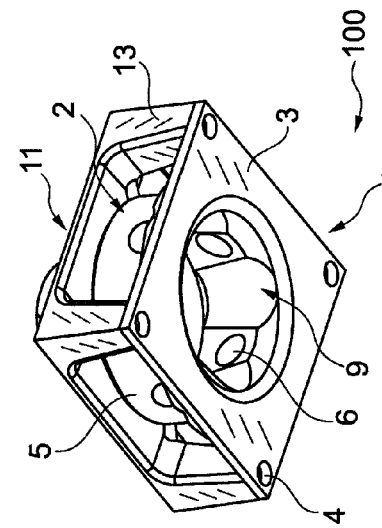
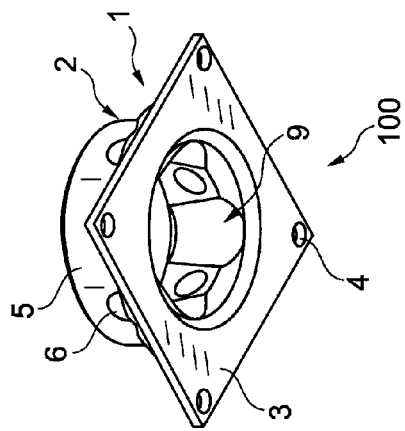
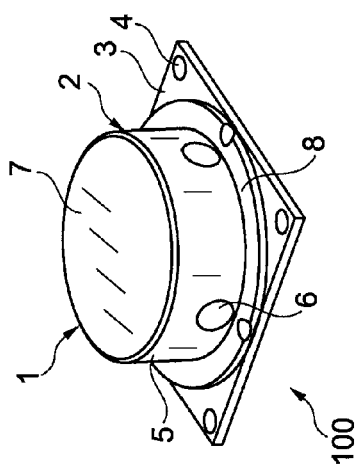

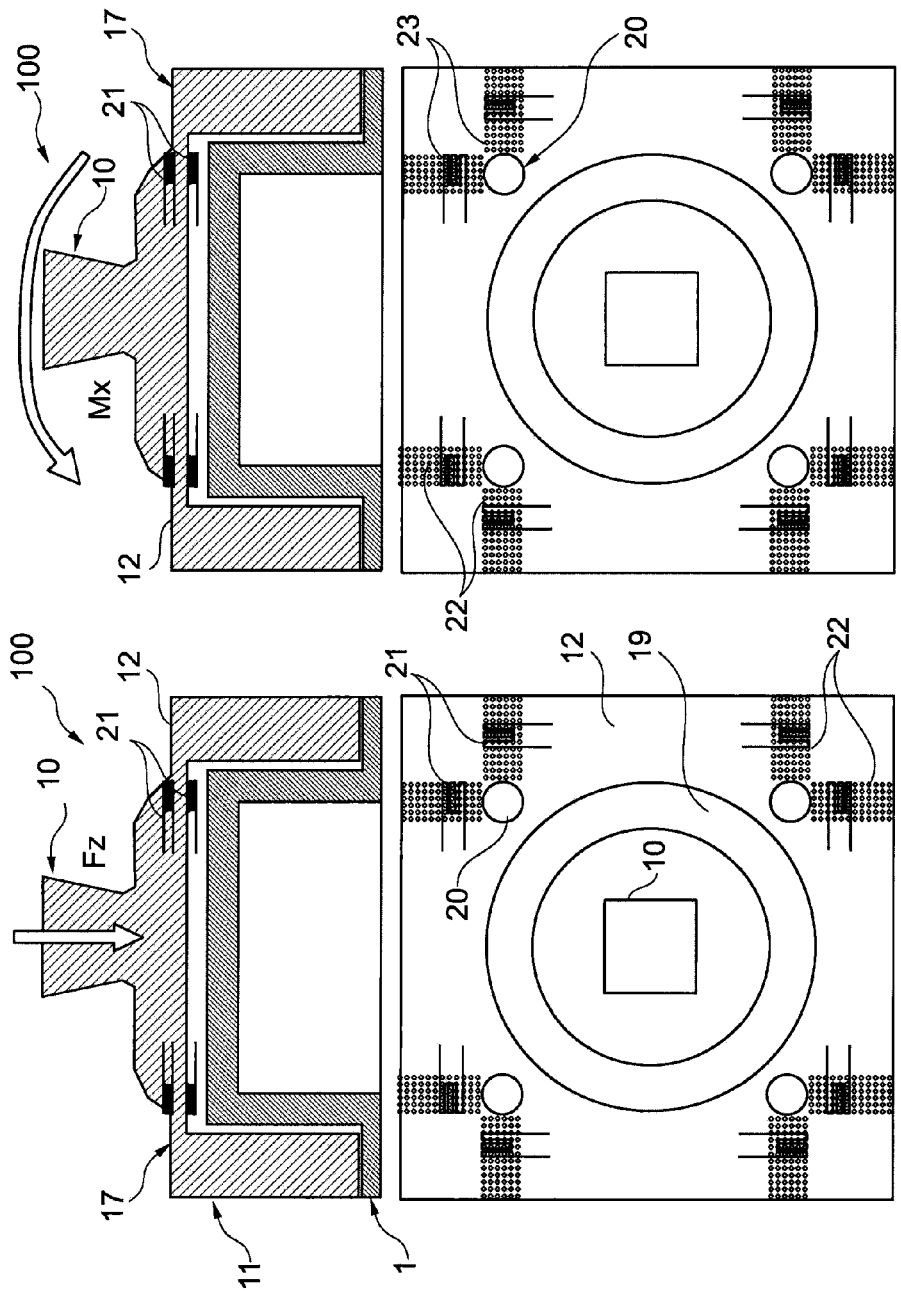

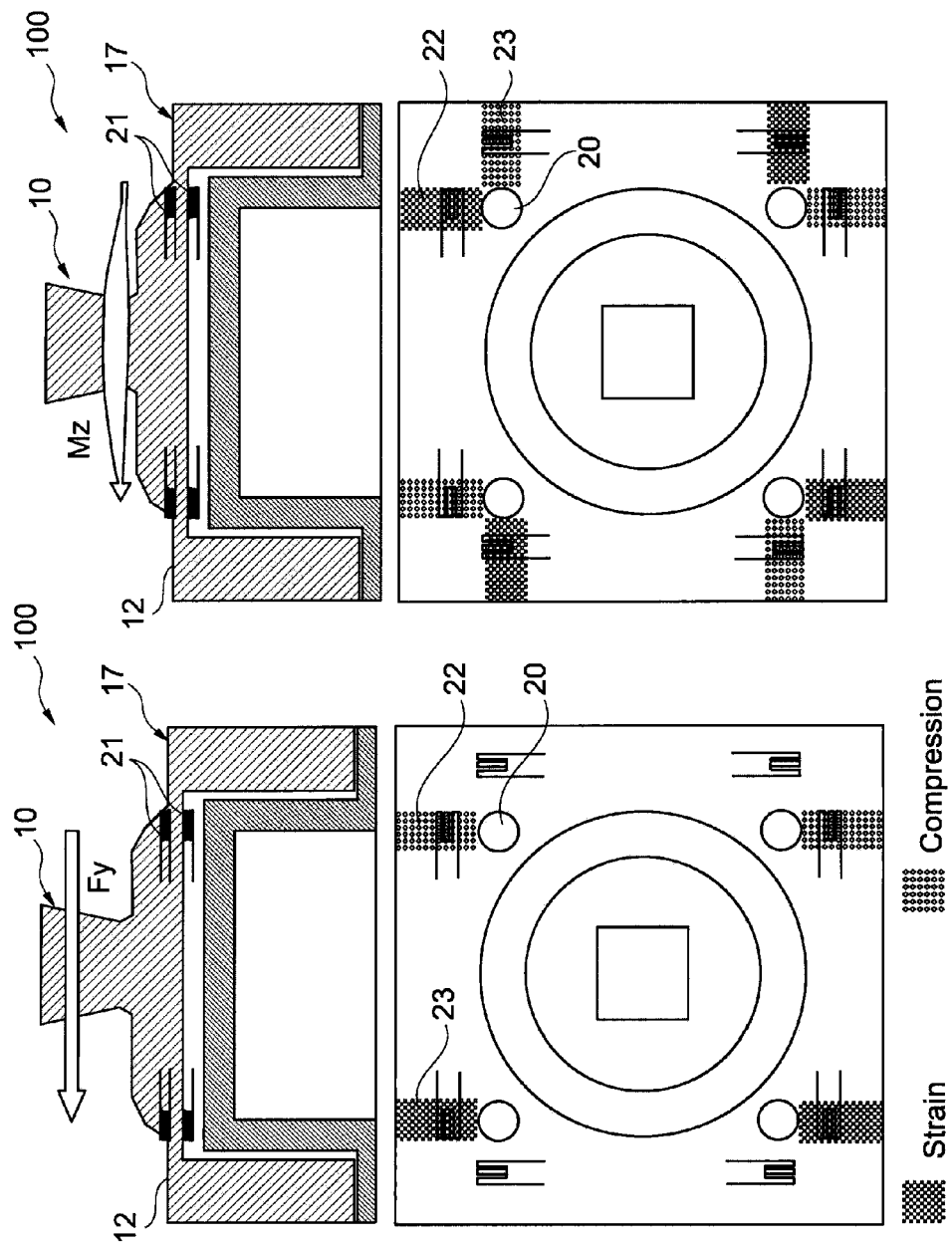

METHOD FOR CARRYING OUT A FUNCTIONAL ANALYSIS OF AN ARTIFICIAL EXTREMITY

CROSS-REFERENCE TO RELATED APPLICATION

This patent application is a national stage application of International Application PCT/DE2006/001767 filed Oct. 10, 2006, which claims priority to German Patent Application No. 10 2005 051 496.0, filed on Oct. 26, 2005. The entire contents of which are hereby expressly incorporated by reference.

TECHNICAL FIELD

The invention relates to a method for carrying out a functional analysis on a person equipped with an artificial extremity formed in a modular fashion with at least one removable functional part.

BACKGROUND

Artificial limbs are in use having highly developed designs. In the case of prostheses for lower extremities including an artificial knee joint, sophisticated technologies are used, which are particularly relevant for safety aspects of the patient. For example, the "walk" and "stand" functions permit safe standing on the one hand and on the other hand permit a motion which is adapted as closely as possible to the natural gait. For this purpose, it is necessary to make it possible for the lower leg to advance completely. Yet, in the process, it is necessary to avoid a heavy impact of the lower leg part on a stopper that limits the extension movement, while considering the patient's usual release force, for example moving the thigh stump. In this case, if applicable, progressive dampers are used which, however, only guarantee the desired function if their damping dosage is correctly set for the respective patient. The same is true for starting the gait cycle from standing and for the transition from walking to safe standing.

The control of the function of such a prosthesis by means of sensors is already known. These sensors determine the transition from one phase of the gait cycle to another phase, or the transition from the gait cycle to a standing movement and vice versa, by means of measured forces, accelerations, torques or the like. These sensors also carry out adjustments of the prosthesis for the next functional phase. An example of such a prosthesis is the leg prosthesis developed and distributed by the Applicant under the name of "C-Leg". However, even such a highly developed prosthesis requires adjustment procedures in order to optimize the adaptation of the prosthesis function to the respective patient. Such adjustments can be undertaken taking into consideration any subjective impressions the patient has when using the prosthesis. In this context, however, it is disadvantageous that the subjective impressions of the patient change and that quantifying the impressions is hardly possible. Hence, optimizing the setting of the prosthesis must be carried out according to the trial-and-error principle, in order to approach an optimized setting.

Apparatuses are known that permit objective standing and gait analysis of the patient fitted with the prosthesis. Complex and thus expensive measuring systems are required for this purpose, which can only be maintained in a few laboratories, for example rehabilitation centers. For the standard fitting of a prosthesis by a prosthetist, such measuring systems are unattainable. Thus, the standard Fitting is carried out without the aid of such measuring systems, that is to say, substantially on the basis of the subjective impressions of the patient.

SUMMARY

The present invention is based on a need for making functional analysis of an artificial extremity possible without complex measuring hardware. In accordance with the invention, this need is achieved by a method in which a sensor assembly, adapted to the dimensions relevant for the installation of a functional part of the prosthesis, is installed in place of that functional part. Forces, accelerations and/or torques are measured by means of the sensor assembly during the use of the artificial extremity and are used to optimize the setting of the basic function of the artificial extremity. The sensor assembly is then replaced by the previously removed functional part while retaining the optimized setting.

Hence, the present invention makes it possible for measurements to be carried out on a completely functional prosthesis that is provided for use by the patient and is fitted to the patient. The patient can thus use the prosthesis for an arbitrary amount of time with the sensor assembly installed, so as to be able to determine, by evaluation of the measured values, whether the setting of the prosthesis can be further optimized. It can also be determined whether, for example, changes in the gait cycle of the patient occur after prolonged use of the prosthesis and thus different settings of the prosthesis would be expedient.

Herein lies the substantial difference to specialized measuring prostheses that are usually used to obtain first measurements of a patient for creating an adequate prosthesis. Such a measuring prosthesis is not customized to the patient and can, therefore, only serve to obtain first indications for the specific patient. By contrast, in accordance with the invention, the prosthesis which was created and completely adapted for the patient is used, said prosthesis having complete functionality with respect to the basic function of the prosthesis.

By means of a sensor assembly constructed in a compact manner for reliably collecting data, it is possible within the scope of the present invention to remove a functional part of the prosthesis provided for an additional function and replace it with the sensor assembly fitted with regard to the functional part's installation dimensions. Of course, the sensor assembly is preferrably designed, in this case, such that the measurements can be taken without utilization of relative motions noticeable during use of the prosthesis. The preferred design of the sensor assembly, therefore, includes strain gauges, piezoelements or the like, in which relative motions or deformations on the order of a fractional amount of a millimeter are sufficient to generate measuring signals.

A rotational adaptor is an example of a removable functional part of a leg prosthesis. It is used directly above the knee joint so as to make rotation of the lower leg relative to the thigh possible, in particular while seated. Use of which, for example, makes a seated posture with crossed legs easier. To carry out the functional analysis, the patient can comfortably do without this additional function, which does not influence the basic function of the leg prosthesis, in particular during the walking process and during the standing condition. In the case of a prosthesis of modular construction, it is of course also possible to shorten a piece of tubing forming the lower leg part or the thigh part by exactly the same amount required for installation of the sensor assembly. When the sensor assembly is removed, a corresponding extension piece can be mounted to the shortened piece of tubing or the shortened piece of tubing can be replaced by a longer piece of tubing.

The functional part replaced by the sensor assembly can also be a carrying modular part, such as, for example, a tube module. Unlike a knee joint or the part of an artificial foot determining the rolling sequence, for example, the basic function of the prosthesis is not determined by the replaced modular part. The sensor assembly can thus also be formed in combination with a remaining modular part, in which the weight and weight distribution should substantially correspond to the replaced modular part. An example of such a sensor assembly is a measuring sensor assembly connected to a remaining lower leg tube, whereby a complete lower leg tube of a leg prosthesis is replaced.

Although the description above has mainly focused on a prosthesis for a lower extremity, it can be readily seen that the invention can also be advantageously used in prostheses for the upper extremities. These include arm prostheses, hand prostheses and shoulder prostheses.

In all cases, additional measurement data, such as, for example, rates of rotation, angular positions and changes in angle, etc., may be acquired. These can either be provided by the sensor assembly itself or by additional sensors placed into the prosthesis.

BRIEF DESCRIPTION OF THE DRAWINGS

In the following text, the invention is explained in more detail with reference to an exemplary embodiment illustrated in the drawings, in which FIG. 1 shows a perspective side view of a first part of a sensor assembly;

FIG. 2 shows a perspective view, from diagonally below, of the first part in accordance with FIG. 1;

FIG. 3 shows a perspective side view of a second part of the sensor assembly;

FIG. 4 shows a perspective view, from diagonally below, of the second part in accordance with FIG. 3;

FIG. 5 shows a perspective side view of the sensor assembly assembled from both parts;

FIG. 6 shows a perspective view, from diagonally below, of the sensor assembly in accordance with FIG. 5;

FIG. 7 shows a schematic sectional view of the sensor assembly for an axial load (z-direction) with a schematic illustration of linear compression regions on a second flange;

FIG. 8 shows an illustration in accordance with FIG. 7 for a torque about a horizontal axis (x-axis);

FIG. 9 shows a schematic illustration in accordance with FIG. 7 for an acting lateral force;

FIG. 10 shows a schematic illustration in accordance with FIG. 7 for a torque about a vertical axis (z-axis);

DETAILED DESCRIPTION

Figure 12:
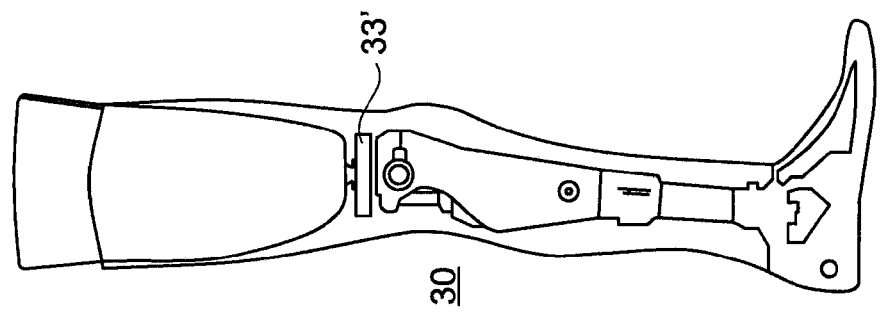
FIG. 12 shows a side view in accordance with FIG. 11, in which the rotational adaptor has been replaced by the sensor assembly in accordance with FIGS. 1 to 10.

FIGS. 1 to 6 show a construction of an exemplary embodiment of an inventive sensor assembly 100 including a first part 1, which is constructed from a hat-shaped cylindrical connection 2 and an adjoining quadratic flange 3. The quadratic flange 3 has through-holes 4 for fixing screws (not illustrated) at its corners.

The hat-shaped cylindrical connection 2 is constructed with a cylindrical lateral wall 5, in which threaded bores 6 are located, separated in each case by an angle of rotation of about 90°. The hat-shaped cylindrical connection 2 has a circular-cylindrical bottom 7 on its top side and an annular brim 8 on its underside, the annular brim 8 being integrally connected to the quadratic flange 3 and strengthening it.

FIG. 2 shows that the hat-shaped cylindrical connection 2 has an approximately rectangular holding space 9, which serves for holding an adjustment adaptor 10 (FIG. 3) which has four inclined adjustment surfaces, against which the adjustment screws, which have been screwed through the threaded bores 6, press.

The adjustment adaptor 10 is formed on a second part 11 of the sensor assembly 100. The second part 11 has a second quadratic flange 12, the dimensions of which correspond to the dimensions of the first quadratic flange 3. The two quadratic flanges 3, 12 are connected to one another by struts 13 which are integrally formed on the second part 11 and which extend downward at the corners of the second quadratic flange 12, so that the struts 13 bear on the first quadratic flange 3, radially outside of the hat-shaped cylindrical connection 2. In each case, the struts 13 are provided with a threaded blind hole 14 on their underside which can be aligned with the through-holes 4 of the first quadratic flange 3.

It can be seen from FIGS. 3 and 4 that the struts 13 have a rectangular cross section and taper off toward their free ends, that is to say downward, by means of an incline 16, which points toward a gap 15 between two struts 13.

The adjustment adaptor 10 is located on a top side 17 of the second quadratic flange 12, which is facing away from the struts 13. It is formed in a known manner in the form of an upside-down pyramidal frustum and thus has four inclined planar adjustment surfaces 18 which can interact with adjustment screws for the purpose of adjustment. The adjustment adaptor 10 merges into a base 19 with an enlarged diameter which creates a transition to the second quadratic flange 12 by means of a bulging plane.

The adjustment adaptor 10 forms a second connection of the sensor assembly 100. In each case, a recess 20 in the form of a through-bore is located between this second connection and the struts 13, which are arranged in the corners of the second quadratic flange 12, and hence in the diagonal direction of the second quadratic flange 12, the recess 20 influencing the formation of stress or strain regions, which is described in more detail below.

FIGS. 5 and 6 show the sensor assembly 100 assembled from the two parts 1, 11 in the assembled state (but without fixing screws). It can be seen that between the holding space 9 of the first connection and the adjustment adaptor 10 forming the second connection, only a small overall height of about 2 to 3 centimeters is required.

FIGS. 7 to 10 in each case schematically show a vertical section through the sensor assembly 100 in accordance with FIGS. 1 to 6, with, however, a schematic illustration of strain gauges 21 adhered to both surfaces of the second quadratic flange 12 as sensor elements.

The plan view located below in each case in FIGS. 7 to 10 shows the positioning of the strain gauges 21 such that their length changes by linear compression regions 22 or strain regions 23, resulting in a changed resistance.

FIG. 7 shows the case of force Fz acting in the z-direction, that is to say in the axial direction of a tubular skeletal prosthesis for a lower leg. The strain gauges 21, located on the top side 17 of the second quadratic flange 12, are in this case located in compression regions 22 which in each case extend in linear fashion, parallel to the edges of the second quadratic flange 12, from the recesses 20 to the adjacent edge. The accordingly aligned strain gauges 21 thus change their resistance value in the direction of compression.

In accordance with FIG. 8, the adjustment adaptor 10 is acted upon by torque about an axis perpendicular to the plane of the drawing (x-direction). For the strain gauges 21 located on the top side 17 of the second quadratic flange 12, the torque leads to compression on the side to which the torque is directed (compare the plotted arrow Mx in FIG. 8), whereas it leads to the formation of strain regions 23 on the opposite side.

FIG. 9 shows a lateral force Fy acting on the adjustment adaptor 10 in the plane of the drawing (y-direction), by means of which strain regions 23 and compression regions 22 are formed only perpendicular to the acting force, while the remaining strain gauges 21 on the top side 17 of the second quadratic flange 12 remain without a measurement signal.

In the case of torque Mz acting in the z-direction illustrated in FIG. 10, a compression region 23 and a strain region 22 are created at each recess 20, with the compression region 23 leading the strain region 22 in each case by 90°, as seen in the direction of the torque Mz.

From the illustrated examples, it can be seen that the different forces and moments that occur can be detected using the strain gauges 21 as sensor elements. The strain gauges 21 on the underside of the second quadratic flange 12 in each case yield signals that are complementary to the signals of the strain gauges 21 on the top side 17 of the second quadratic flange 12, so that these can contribute to an amplified measurement signal in the case of a suitable addition.

Figure 11:
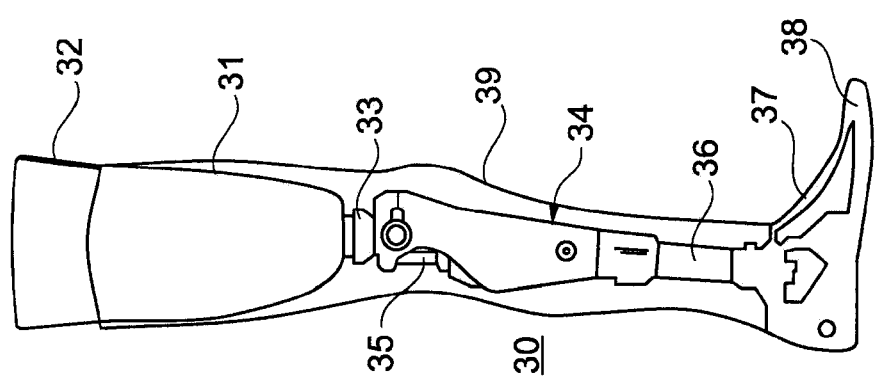
FIG. 11 shows a side view of a leg prosthesis with a rotational adaptor.

FIG. 11 shows a known leg prosthesis 30 with a holding funnel or socket 31 for a thigh stump. A skin-friendly liner 32 is fitted in the socket 31 and creates a comfortable contact with the thigh stump.

A rotational adaptor 33 is connected to the lower end of the socket 31 by means of a conventional adjustment pyramid (such as adjustment adaptor 10 in FIGS. 1-6). The connection of the rotational adaptor 33 to a lower leg part 34 is likewise carried out by means of an adjustment pyramid.

The lower leg part 34 is formed as a computer-controlled prosthesis part, as is known under the name of "C-Leg" from Otto Bock HealthCare GmbH. The lower leg part 34 comprises a polycentric knee joint 35, which is in the form of a known four-bar linkage. A modular tube 36 is connected to the bottom of the lower leg part 34 and creates a connection to an artificial joint-free foot 37, the possible construction of which is likewise known and does not have to be explained in any more detail here. Both the artificial foot 37 and the leg prosthesis 30 are provided with a cosmetic covering 38, 39.

The main function of the prosthesis 30 is to permit a gait that is as natural as possible, safe standing, and comfortable sitting down for the individual user of the prosthesis 30. The rotational adaptor 33 is locked during the main function of the prosthesis 30 and can be unlocked when there is no load acting on the lower leg part 34. By means of the rotational adaptor 33, the lower leg of the prosthesis 30 can be rotated with respect to the thigh, in particular when the user of the prosthesis 30 is sitting.

To fit the prosthesis 30, and to check the prosthesis 30 at a later stage (if applicable), the rotational adaptor 33 can be replaced by a sensor assembly (in this case designated by 33'), in accordance with the present invention as explained in FIGS. 1 to 10. By replacing the rotational adaptor 33 with the sensor assembly 33', the basic function of the prosthesis 30 remains unchanged if the installation dimensions of the sensor assembly 33' correspond to those of the rotational adaptor 33. Only the additional function of rotating the lower leg with respect to the thigh is lost. However, the main function of the prosthesis 30, namely the behavior during walking, standing and sitting down, is not impaired. The data required to evaluate the function of the prosthesis 33 can therefore be determined by means of the sensor assembly 33', said prosthesis 30 having been customized for the patient and being fully functional. In this case, the sensor assembly 33' can be used both for the first fit of the prosthesis, that is to say for short-term use, and likewise for long-term examination of the movement of the patient with the prosthesis 30, which has been fitted and adjusted especially for him/her.

The invention claimed is:

1. A method for carrying out a functional analysis on a person equipped with an artificial extremity having adjustable settings and a removable part, the method comprising the steps of:
   providing a sensor assembly configured as a replacement for the removable part of the artificial extremity;
   installing the sensor assembly in place of the removable part;
   measuring at least one of forces, accelerations and torques with the sensor assembly during use of the artificial extremity by the person;
   optimizing the adjustable settings of the artificial extremity based on the measurements of the sensor assembly; and
   removing the sensor assembly and installing the removable part back into the artificial extremity, while retaining the optimized settings.

2. The method of claim 1, wherein a first function of the artificial extremity is able to be adjusted based on the adjustable settings.

3. The method of claim 2, wherein the artificial extremity is formed in a modular fashion, including at least one removable functional part that provides a function in addition to the first function.

4. The method of claim 3, wherein the step of providing a sensor assembly further comprises configuring the sensor assembly with dimensions and connections consistent with the removable functional part and wherein the removable part of the artificial extremity comprises the removable functional part.

5. The method of claim 1, wherein the artificial extremity comprises a leg prosthesis.

6. The method of claim 5, wherein the leg prosthesis includes a rotational adaptor arranged above an artificial knee joint and wherein the sensor assembly is configured as a replacement for the rotational adaptor in the leg prosthesis.

7. A method for carrying out a functional analysis on a person equipped with an artificial extremity, a first function of the artificial extremity being able to be adjusted, with the artificial extremity being formed in a modular fashion, the artificial extremity including at least one removable functional part that provides a function in addition to the first function, the method comprising the steps of:
   providing a sensor assembly configured as a replacement for the removable functional part;
   installing the sensor assembly in place of the removable functional part;
   measuring at least one of forces, accelerations and torques with the sensor assembly during use of the artificial extremity by the person;
   optimizing adjustment settings of the first function of the artificial extremity based on the measurements of the sensor assembly; and
   reinstalling the removable functional part into the artificial extremity in place of the sensor assembly while retaining the optimized settings.

8. The method of claim 7, wherein the artificial extremity comprises a leg prosthesis.

9. The method of claim 8, wherein the leg prosthesis includes a rotational adaptor arranged above an artificial knee joint, and wherein the sensor assembly is configured as a replacement for the rotational adaptor in the leg prosthesis.

10. The method of claim 7, wherein the removable functional part includes dimensions and connections, and the sensor assembly has the same dimensions and connections as the removable functional part.

* * * * *